(12) United States Patent
Knight et al.

(10) Patent No.: US 12,251,543 B2
(45) Date of Patent: Mar. 18, 2025

(54) VARIABLE LENGTH INJECTION SYRINGE

(71) Applicant: Becton, Dickinson and Company, Franklin Lakes, NJ (US)

(72) Inventors: John Knight, Lincoln, NE (US); Jeffrey Reed, Minden, NE (US); Scott Townsend, Holdrege, NE (US); Patrick McCallum, Franklin Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/631,812

(22) PCT Filed: Jul. 29, 2020

(86) PCT No.: PCT/US2020/044059
§ 371 (c)(1),
(2) Date: Jan. 31, 2022

(87) PCT Pub. No.: WO2021/025922
PCT Pub. Date: Feb. 11, 2021

(65) Prior Publication Data
US 2022/0273888 A1  Sep. 1, 2022

Related U.S. Application Data

(60) Provisional application No. 62/882,277, filed on Aug. 2, 2019.

(51) Int. Cl.
*A61M 5/32* (2006.01)
*A61M 5/46* (2006.01)

(52) U.S. Cl.
CPC ........ *A61M 5/3269* (2013.01); *A61M 5/3245* (2013.01); *A61M 5/3275* (2013.01);
(Continued)

(58) Field of Classification Search
CPC .............. A61M 5/3202; A61M 5/3245; A61M 5/3269; A61M 5/3275
See application file for complete search history.

(56) References Cited

U.S. PATENT DOCUMENTS

| 4,356,822 A | 11/1982 | Winstead-Hall |
| 4,935,013 A | 6/1990 | Haber et al. |

(Continued)

FOREIGN PATENT DOCUMENTS

| CN | 1946445 A | 4/2007 |
| CN | 213284973 U | 5/2021 |

(Continued)

OTHER PUBLICATIONS

International Search Report dated Nov. 9, 2020, which issued in the corresponding PCT Patent Application No. PCT/US2020/044059.

*Primary Examiner* — Nathan R Price
*Assistant Examiner* — Tania Ismail
(74) *Attorney, Agent, or Firm* — Dickinson Wright PLLC

(57) ABSTRACT

A syringe assembly includes a syringe barrel (12) having a proximal end and a distal end, a needle hub (20) supporting the needle and coupled to the distal end of the syringe barrel (12). A moveable shield (36) is included for sliding from a first position where the needle is exposed a first length, a second position where the needle is exposed a second length less than said first length, and a third position covering a distal end of the needle. A locking mechanism (48, 86) is included to retain the shield in the second position while enabling the shield to slide to the third position, and to lock the shield in the third position to prevent re-use of the syringe.

10 Claims, 8 Drawing Sheets

(52) U.S. Cl.
CPC ............ *A61M 5/46* (2013.01); *A61M 5/3202* (2013.01); *A61M 2005/3247* (2013.01); *A61M 2005/3254* (2013.01); *A61M 2205/581* (2013.01); *A61M 2205/582* (2013.01)

(56) References Cited

U.S. PATENT DOCUMENTS

| | | |
|---|---|---|
| 5,156,599 A | 10/1992 | Ranford et al. |
| 5,498,244 A | 3/1996 | Eck |
| 7,566,324 B2 | 7/2009 | Hommann et al. |
| 2005/0203459 A1 | 9/2005 | Alchas |
| 2011/0208126 A1 | 8/2011 | Riemelmoser |
| 2011/0251587 A1* | 10/2011 | Banik ................. A61M 5/3287 604/117 |
| 2013/0310744 A1 | 11/2013 | Brereton et al. |
| 2015/0174339 A1 | 6/2015 | Bokelman et al. |
| 2017/0216534 A1 | 8/2017 | Kawabe et al. |
| 2018/0221591 A1 | 8/2018 | Calvert |

FOREIGN PATENT DOCUMENTS

| | | |
|---|---|---|
| JP | 2007-521845 A | 8/2007 |
| JP | 2007-528274 A | 10/2007 |
| JP | 2014-503285 A | 2/2014 |
| WO | 2016-021323 A1 | 2/2016 |
| WO | 2018/170893 A1 | 9/2018 |

* cited by examiner

VARIABLE LENGTH INJECTION SYRINGE

This application is a 371 application of PCT/US2020/044059 filed on Jul. 29, 2020, which claims priority under 35 USC § 119(e) from U.S. Provisional Patent Application Ser. No. 62/882,277 filed on Aug. 2, 2019, the disclosure of which is incorporated herein by reference in its entirety.

FIELD OF THE INVENTION

The present invention is directed to a syringe having a movable member for modifying the length of the exposed portion of a syringe needle for aspirating and filling the syringe for injecting a medication into a patient. The syringe includes the movable member to vary the effective length of the syringe for the injection to a desired depth and for shielding the needle after use.

DESCRIPTION OF THE RELATED ART

Needle lengths in the range of 4 mm to 6 mm are inserted into a container or vial and aspirate due. The needle length requires the needle to pierce a septum in the vial in a straight line to ensure penetration and reduce the risk of the needle bending.

The insertion of a needle into the skin of a patient is determined primarily by the features of the needle and not the features or structure of the needle support. Needle insertion into the skin of patient is generally classified into three phases that influence the injection depth. The first phase corresponds to the initial contact of the needle with the skin where the tissue deforms without puncturing the surface of the skin. A second phase refers to the puncture of the skin and the relaxation of the skin when the insertion force of the needle is stopped. The third phase is where the needle is extracted and pulls or stretches the skin outward as the needle is extracted.

Needle lengths, such as needles having a length of about 4 mm to 6 mm are adapted to inject a medication to a specified target depth in a subcutaneous region. The present invention provides a structure so that a needle can be consistently inserted to a desired target depth. Prior injection devices have the needle or cannula supported on an axial post extending from a hub. The post forms a narrow portion and a relatively wider base that does not contact the skin during the injection. In other injection delivery devices, a distal face of the hub placed against the injection site may be relatively large, and may be provided with a slight taper at the edge. The edge of the hub can engage the skin when the cannula is inserted at an angle relative to the surface of the skin of the patient.

Various injection devices have been produced where the supporting structure does not contact the skin during injection or extraction of the needle. Other devices have been proposed where the end face of the device is positioned to contact the surface of the skin to limit the depth of penetration into the patient.

Injector delivery devices facilitate self-administration of parenteral medications. An example of delivery device is pen needle. Needles are a component of needle-based injection systems and includes a doubled ended cannula assembled into a plastic hub using an adhesive. A hub having internal threads allows the hub to attach to the pen-injector device. The needle attachment allows the proximal end of cannula to penetrate through the rubber septum of the medicament cartridge to create the fluid flow path. For many diabetics maintaining blood glucose control is achieved by performing multiple daily injections of insulin into the subcutaneous (SC) tissue using pen injector delivery devices developed to be a convenient, discreet alternative to the vial and syringe. Numerous injectors are commercially available in either disposable or multi-use configurations, each offering various patient-centric features. The distal pen needle cannula interfaces with the delivery site providing a conduit for delivery. Delivery devices and needle designs are intended to enable consistent delivery to the target tissue space, minimize leakage of the injected substance, and reduce pain/discomfort and site effects such as bleeding and bruising associated with the injection. The primary design features, needle length/gauge and hub face geometry, in conjunction with mechanics of the delivery system and injection technique, dictate injection success.

Injections may be performed in the intradermal region, the subcutaneous region and the intramuscular (IM) region of the skin. For many types of injectable medications, including insulin, the SC region is preferred for administering an injection.

While the prior devices are generally suitable for the intended use, there is a continuing need for improved devices for controlling the depth of penetration of a cannula for delivering a drug or medicament to a selected target area.

SUMMARY

The present syringe assembly is directed to a device to assist in aspirating a syringe and injecting a medication to a selected depth into the patient. In one embodiment a syringe includes a needle with a first exposed length for aspirating the syringe and a second exposed length for injecting the substance to the desired depth into the patient. The syringe assembly can also include a movable shield that moves over the end of the needle after use and locks in an extended position to avoid accidental needle stick.

The syringe in one embodiment includes a syringe barrel and a needle or cannula extending from the distal end of the syringe barrel. A movable shield is coupled to the syringe for sliding movement relative to the syringe. The movable shield slides between a retracted position where the needle is exposed a length suitable for filling and aspirating the syringe and an extended position extending at least partially over the needle to limit the exposed length of the needle for injection into the patient. A base forms a mounting member for coupling to the syringe where the movable shield slides relative to the base to slide over at least a portion of the needle extending from the syringe during aspiration and during an injection. The moveable shield slides relative to the syringe from a retracted position so that the needle has an exposed length that is able to pierce a septum on the container or vial for aspirating the syringe. The movable shield is able to slide to a second position exposing a selected length of the needle corresponding to a desired depth of penetration. After the injection is completed, the movable shield slides to an extended and locked position covering the needle after use. The shield and/or the base can include one or more locking mechanisms to lock the shield in the extended position to cover the needle after use.

In one embodiment, the syringe includes a syringe barrel and a shield coupled for sliding with respect to the syringe from a first position where the needle is exposed a first length, a second position where the needle is exposed a second length less than the first length, and a third position where the shield completely covers the tip of the needle.

In another embodiment, the syringe includes a syringe barrel with a shield attached to a distal end of the syringe.

An arm forming a connecting member is coupled to the shield for sliding the shield between a retracted position to expose a length of the needle on the syringe, and an extended position covering the needle. The arm is configured to slide on a base that is coupled to the syringe to hold the shield in one or more selected positions relative to the syringe and the needle on the syringe.

In one embodiment, the syringe has a shield that slides with respect to the syringe between a retracted position to expose a length of the needle for filling the syringe and injecting the medication into the patient to a selected depth, a second position covering only a portion of the needle for injecting the medication to a depth less than when the shield is in the first position, and an extended position where the shield covers the needle and where the shield locks in the extended position to prevent re-use of the syringe. A locking mechanism can be included to retain the shield in the second position during use while enabling the shield to slide to the extended position where the shield permanently locks to prevent further movement of the shield.

Another feature of the syringe is a moveable shield coupled to a base for sliding movement relative to the syringe where the base is coupled to the outer surface of the syringe. The shield and/or base have a locking mechanism for retaining the shield in a partially retracted position where the locking mechanism can release the shield from the partially retracted position by applying a manual force to the shield where the shield can slide to an extended position to cover the distal end of the needle and permanently lock in the extended position.

The features are basically attained by a syringe assembly comprising a syringe barrel having a proximal end and distal end, a needle bearing hub coupled to said distal end of the syringe barrel, and a moveable shield member positioned on the syringe barrel. The moveable shield member is mounted for sliding between a first position where the needle is exposed, a second position covering at least a portion of the needle, and a third position where the needle is completely covered by the shield.

The features of the syringe include a syringe barrel having a proximal end and a distal end, a needle-bearing hub coupled to said distal end of the syringe barrel, and a shield that slides relative to the syringe to cover the distal end of the needle after use and lock the shield in the extended position to prevent re-use. The shield assembly includes a base coupled to the syringe and has a locking member projecting outward from the base. The shield has a sleeve with a dimension for covering the end of the needle and an arm that couples with the base to allow the shield to slide relative to the base. The arm includes a first locking member that mates with the locking member of the base to retain the shield in a partially extended position to provide a short needle length. The locking member can be released by pushing on the shield or arm in the distal direction with respect to the syringe to slide the shield over the end of the needle where the locking member on the base engages a second locking member on the arm to lock the arm and shield in the extended position and prevent the shield from sliding in the retracted or proximal direction with respect to the syringe.

A method is provided for aspirating and filling a syringe assembly, preparing the syringe assembly for use, and preventing re-use of the syringe. The method comprises providing a syringe having a proximal end and a distal end, a needle-bearing hub coupled to the distal end of said syringe, and a movable shield coupled to the syringe. The shield is in a first position exposing a first length of the needle having a first length for filing the syringe. The shield slides to a second position to expose a second portion of the needle having a second length less than the first length for injecting the medication to the patient, where the shield is releasably retained in the second position. The shield then slides to a third extended position to cover the end of the needle and locks in the extended position to prevent re-use of the syringe.

These and other features of the invention will become apparent from the following detailed description of the invention, which in conjunction with the drawings disclose various embodiments of the syringe.

BRIEF DESCRIPTION OF THE DRAWINGS

The following is a brief description of the drawings in which.

DETAILED DESCRIPTION OF THE EMBODIMENTS

Figure 1:
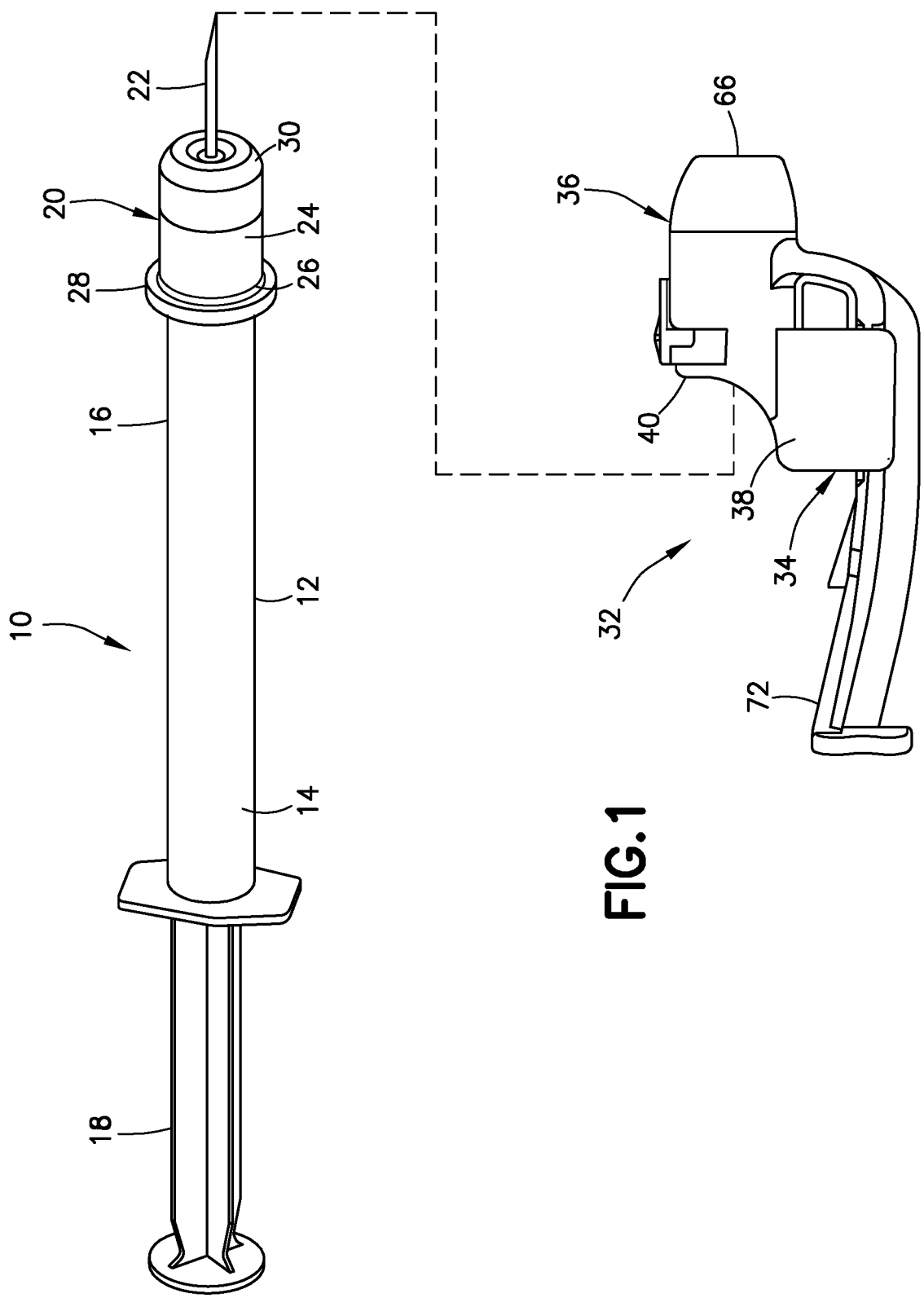
FIG. 1 is a side view of the syringe assembly in one embodiment.

The syringe assembly of the invention refers to a syringe having a needle or cannula for injecting a medication or other substance into a patient. The terms needle and cannula are used herein interchangeably to refer to a thin tubular member having a sharp end for insertion into an injection site on a subject. A distal direction is in the direction toward the injection end of the syringe assembly, and the proximal direction is the opposite direction. The axial direction refers to a direction along or parallel to the longitudinal axis of the needle and the needle hub and the radial direction refers to a direction perpendicular to the axial direction.

The syringe is configured to injecting a medication into a patient at a selected depth depending on the medication and the intended depth of penetration. The intradermal layer in adults generally has a thickness of around 2 to 3 mm, so that intradermal injection depth is in a range of up to about 3 mm as measured from the outer surface of the skin. The thickness of the subcutaneous layer varies depending on the age of the patient, gender, body mass index (BMI), and the part of the body where the injection is administered. The subcutaneous region has an average thickness of about 7 mm to about 15 mm. Insulin can be delivered to the subcutaneous region.

The syringe is suitable for use in a method for injections and for injecting a drug to a patient. The description of the embodiments is not to be deemed as limiting. The disclosure is intended to enable the artisan of ordinary skill to practice variants of the syringe described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

This disclosure is not limited in its application to the details of construction and the arrangement of components set forth in the following description or illustrated in the drawings. The embodiments herein are capable of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are to aid illustration, but are not limiting. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the structure. Distal refers to a direction or position toward the patient end of the needle and proximal refers to a direction or position away from the patient end of the needle and toward the user of the syringe.

Referring to the drawings, the syringe 10 includes a syringe barrel 12 having a proximal end 14 and a distal end 16. The proximal end 14 receives a movable plunger 18 and stopper for dispensing the substance contained in the syringe assembly.

A needle hub 20 is coupled to the distal end 16 of the syringe barrel 12 as shown in FIG. 1. The needle hub 20 includes a needle 22 extending axially from the needle hub and the syringe. The needle hub 20 is configured for coupling to the distal end of the syringe barrel 12. In the embodiment shown, the needle hub 20 has a substantially cylindrical body 24 with a proximal end 26 having outwardly extending radial flange 28 and a distal end 30.

Figure 5:
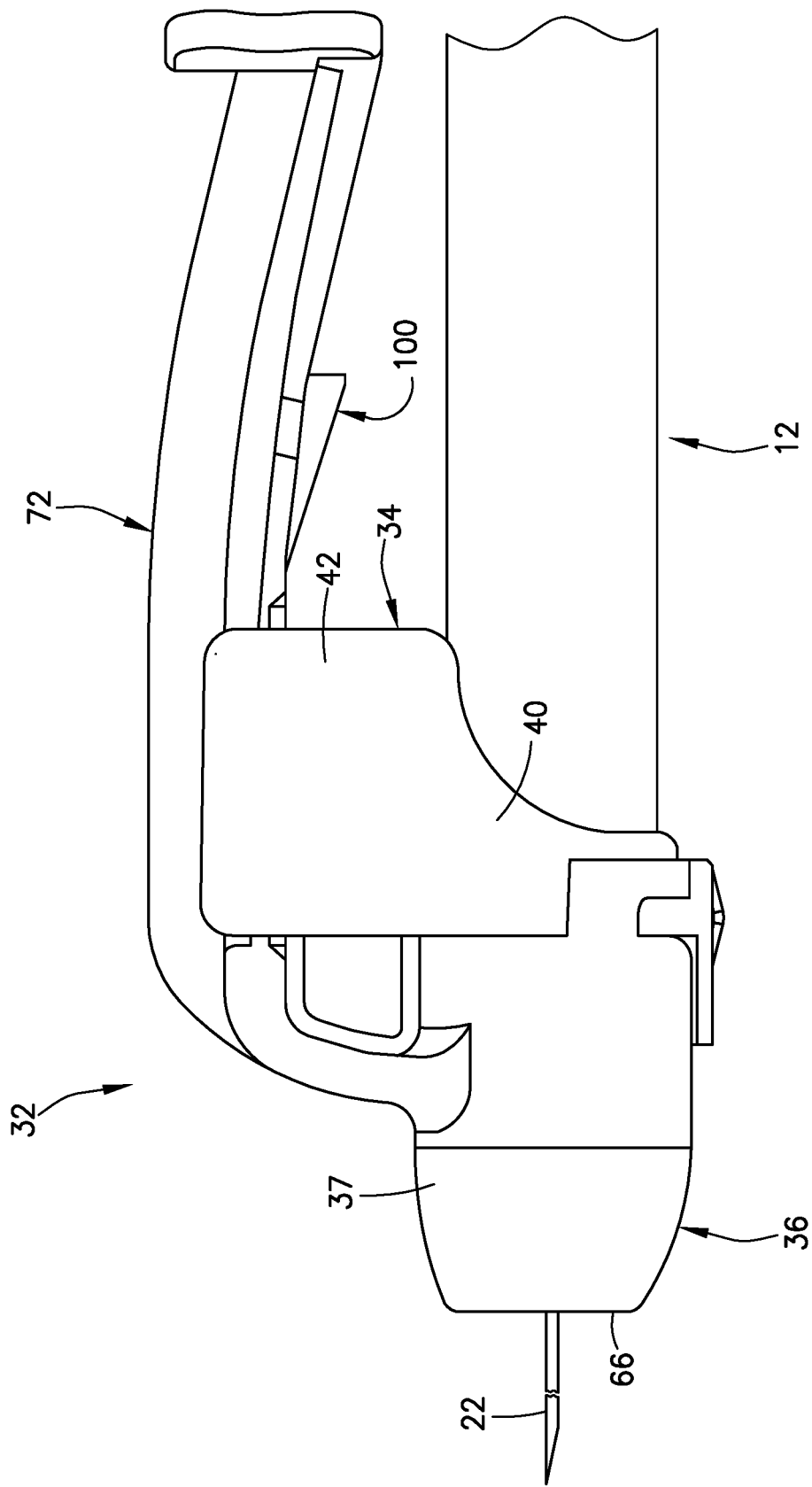
FIG. 5 is a side view of the shield in the initial position.
Figure 7:
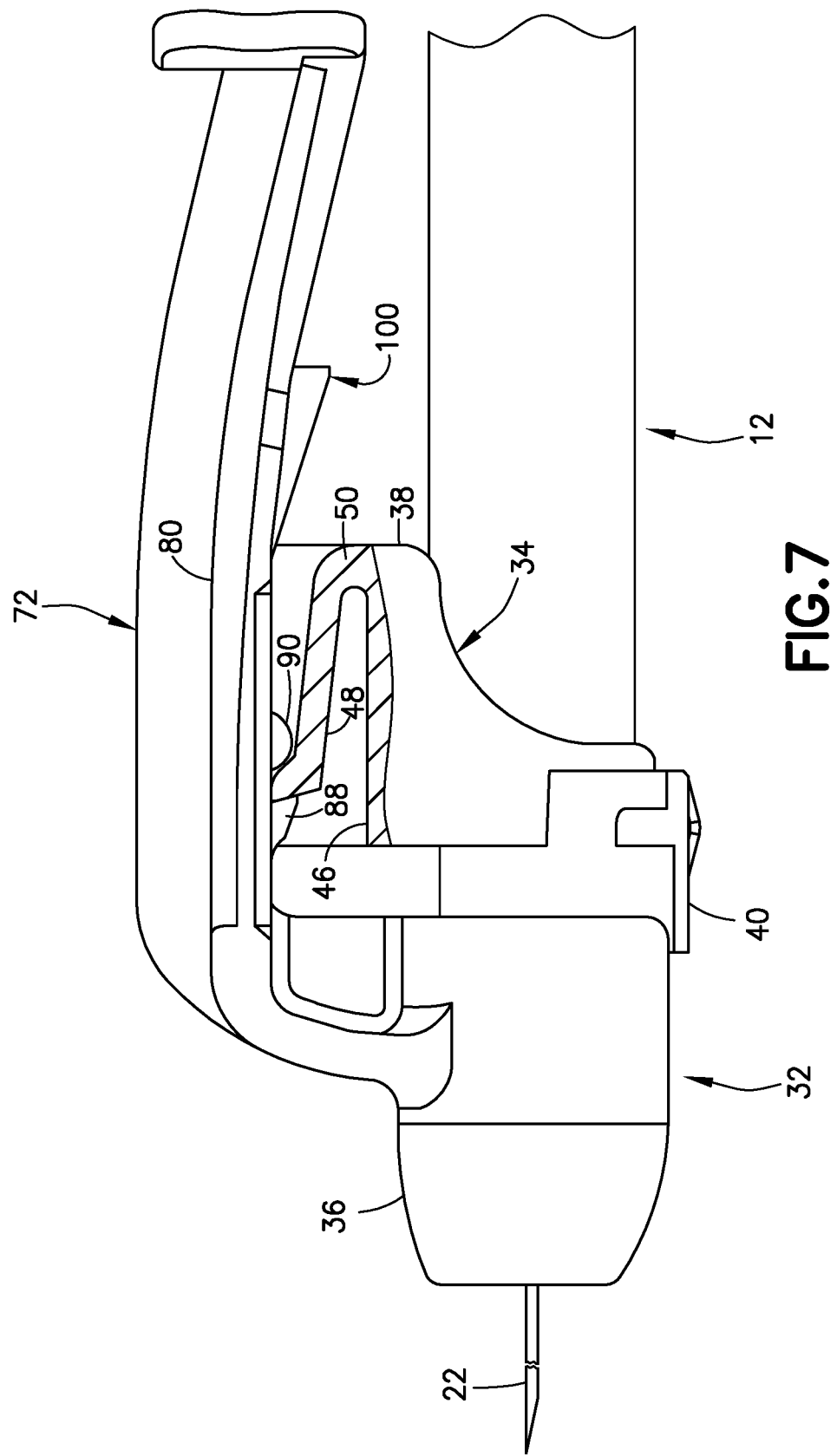
FIG. 7 is a partial cross-sectional side view of the shield in the partially extended position.
Figure 8:
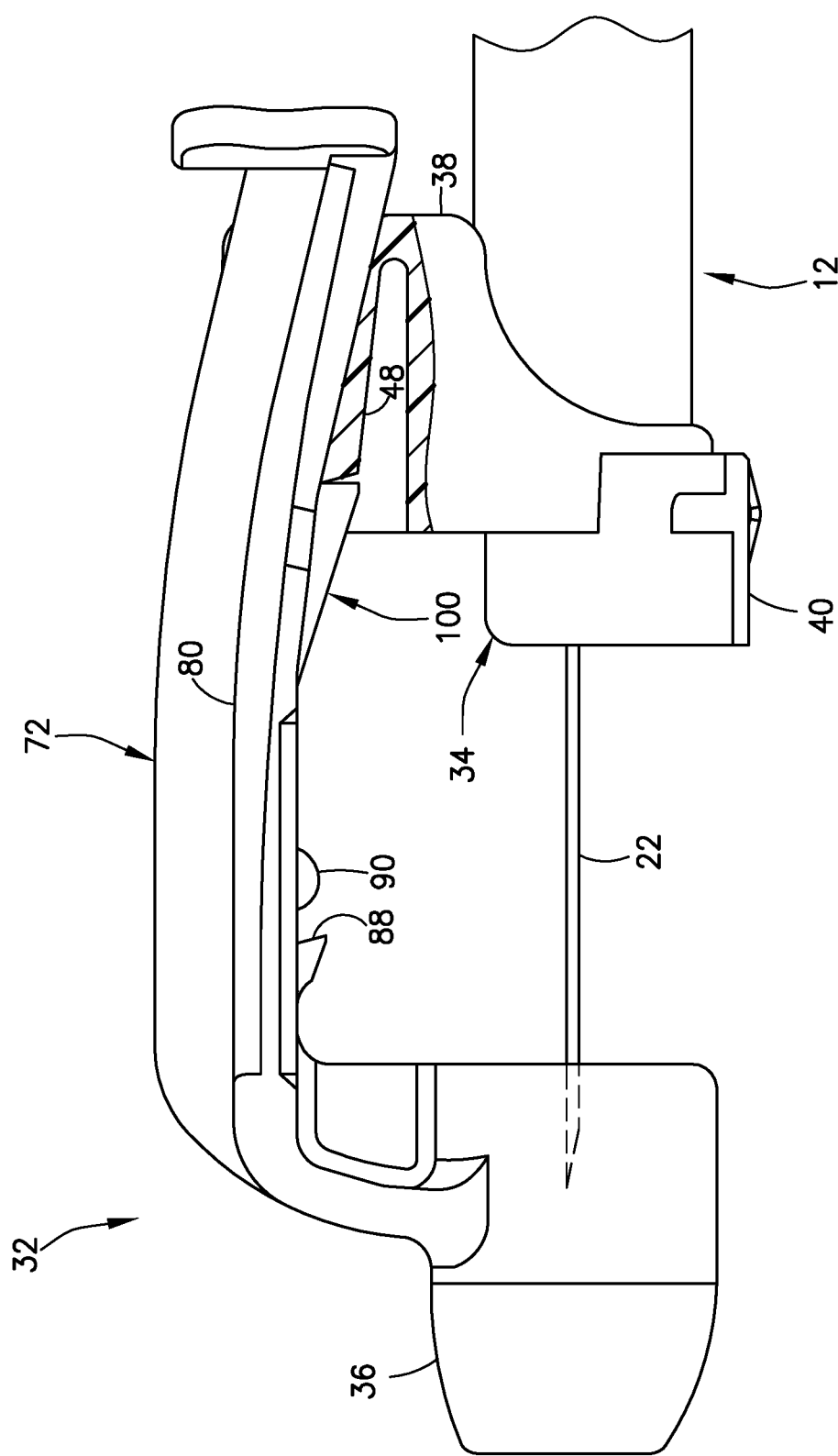
FIG. 8 is a partial cross-sectional side view of the shield in the extended position covering the needle.

A needle shield assembly 32 is coupled to the syringe for sliding from an initial retracted position shown in FIG. 5 to an intermediate position shown in FIG. 7, and to an extended position to cover the distal end of the needle after use to prevent re-use of the syringe and prevent inadvertent needle stick shown in FIG. 8. The needle shield assembly 32 includes a base 34 for coupling to the syringe and a movable shield 36 for covering the needle after use. In the embodiment shown, the movable shield 36 slides relative to the base 34 and with relative to the syringe 12.

Figure 4:
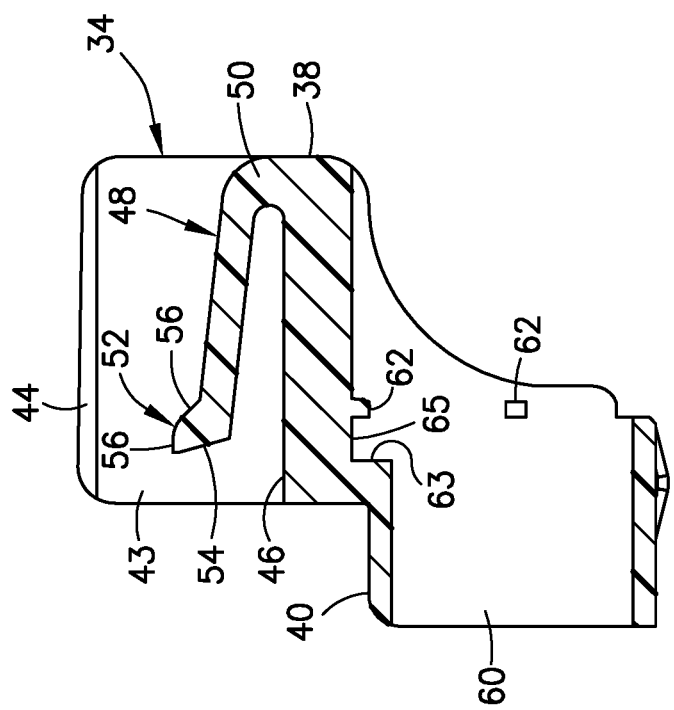
FIG. 4 is a cross-sectional view of the base of the shield assembly.
Figure 3:
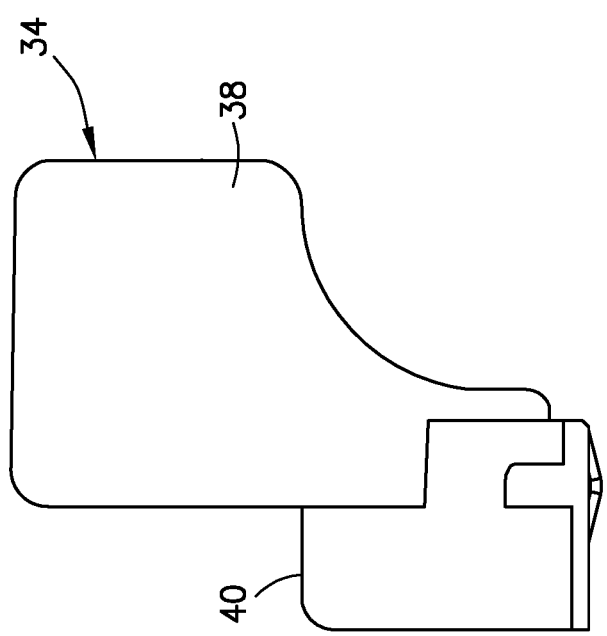
FIG. 3 is a side view of the base of the shield assembly.

Referring to FIGS. 3 and 4, the base 34 is configured for coupling to the syringe and for enabling the shield 36 to slide with respect to the base 34 and with respect to the syringe and needle. The base 34 in the embodiment shown is coupled to the syringe hub 20 by snapping onto the radial flange 28. The base 34 forms a mounting structure for the shield and for coupling the shield to the syringe for sliding movement to different positions on the syringe and with respect to the needle. The base 34 includes a body 38 and a mounting member shown as a cylindrical sleeve 40. The body 38 is configured for receiving and attaching to the shield so that the shield can slide in a longitudinal direction with respect to the syringe and the base. The sleeve 40 has a configuration for coupling to the syringe barrel 12. In the embodiment shown, the sleeve 40 has a substantially cylindrical shape with a central opening with a dimension for coupling with the syringe barrel. The sleeve 40 is attached to the syringe barrel to resist axial movement and separation of the sleeve with respect to the syringe barrel 12 during normal use. The sleeve 40 can be coupled directly to the syringe in a manner where the shield can rotate on the syringe to a position selected by the user. In one embodiment, the sleeve 40 is fixed to the syringe barrel 12 by a suitable mechanical mechanism or by bonding such as by an adhesive or welding.

The base 34 includes a pair of spaced apart side walls 42 forming a longitudinal passage 43 or gap for receiving the shield and allowing the shield to slide longitudinally in the passage 43. The side walls 42 have a top end with inwardly projecting flanges 44 extending in the longitudinal direction. A bottom wall 46 extends between the side walls 42 forming the passage 43 to form an open portion between the side walls 42 that is open to a top end of the base. The flanges 44, side walls 42 and bottom wall 46 capture the shield 36 for sliding movement relative to the syringe and needle.

A locking mechanism is included in the base 34 for retaining the shield in one or more selected positions with respect to the base and the syringe. In the embodiment shown, the locking mechanism is in the form of a latch to retain the shield 36 in a selected position where the latch can be released to allow the shield to slide to another position in the proximal direction. The locking mechanism in the embodiment shown is a spring biased finger 48 having a proximal end connected to the base 34 by a spring hinge 50 to enable the finger 48 to bend inwardly toward the bottom wall 46 of the base 34 and bias the finger 48 outwardly away from the bottom wall of the base. The finger 48 has a distal end with a tab 52 having a distal face 54 and proximal face 56. As shown in FIG. 4, the distal face 54 defines a leading face of the finger 48. The proximal face 56 in the embodiment shown is inclined relative to the longitudinal axis of the base 34 and inclined outwardly in a distal direction. A substantially flat end face 56 of the tab 52 is shown substantially parallel to the longitudinal axis of the finger 48 and the longitudinal axis of the base 34.

The sleeve 40 is configured for coupling the base 34 to the syringe and mounting the shield 36 for sliding movement with respect to the base and the syringe. The sleeve 40 has a center opening 60 extending longitudinally with a dimension for receiving the distal end of the syringe. A coupling mechanism is included in the central opening 60 shown in FIG. 4 for coupling the sleeve 40 to the syringe. The coupling mechanism can be one or more detents 62 on the inner surface of the sleeve that project inwardly to engage and capture the flange 28 on the needle hub. The detents 62 are spaced longitudinally from an end wall 63 to form a recess 65 to receive and capture the flange 28 on the syringe barrel 12. In one embodiment, the coupling mechanism can be a snap connection that inhibits or prevents separation of the base 34 from the syringe barrel 12 and the needle hub 20. The detent 62 as shown in FIG. 4 can have an angled or slanted proximal face to slide over the radial flange 28 of the syringe. In other embodiments, coupling mechanism can be an annular ring that can form a snap or interference connection.

The sleeve 40 in the embodiment shown has an open proximal end to receive the distal end of the needle hub and radial flange 28 when the base 34 is coupled to the needle hub or syringe. In one embodiment, the sleeve has a shape and dimension to receive the distal end of the needle hub where the needle can extend distally from the distal end of the sleeve. The passage 60 can be open at the distal end as shown in FIG. 4 where the distal end 30 of the needle hub can project from the distal end of the sleeve 40. In one embodiment, the sleeve 40 has a longitudinal length complementing the length of the needle hub so that the distal end 30 of the needle hub is aligned with the distal end of the sleeve. Alternatively, the distal end 30 of the needle hub can be recessed slightly with respect to the distal end of the sleeve. In other embodiments the sleeve can have an end wall with an opening having a dimension to allow the needle to pass through and contact the distal end of the needle hub.

Figure 2:
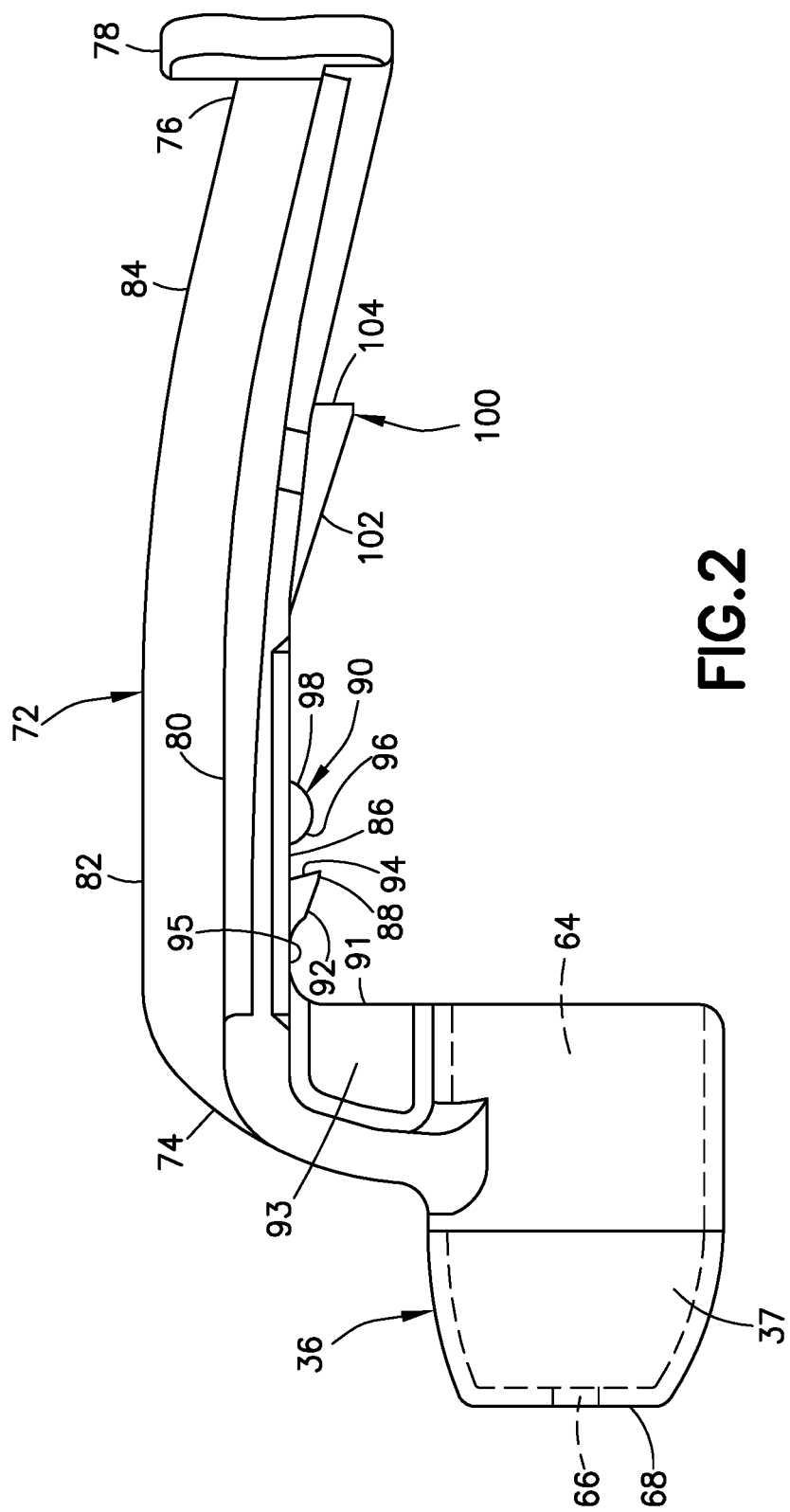
FIG. 2 is a side view of the shield of the shield assembly of FIG. 1.

The shield 36 as shown in FIG. 2 has a shield body 37 with a substantially cylindrical shape and an open axial passage 64 having an open proximal end 66 and a distal end wall 68. The end wall 68 has a central opening 70 with a dimension to allow the needle to extend through the shield 36 a sufficient length to fill and aspirate the syringe and to inject the medication into the patient. The open proximal end 66 has a dimension to receive the distal end of the sleeve 40 where the end of the sleeve 40 can slide into the open proximal end 66 as shown in FIG. 5.

The shield 36 includes an arm 72 attached to a side of the shield 36 and extending in the proximal direction of the shield and spaced radially outward from the wall of the shield with respect to the center axis of the shield 36. The arm 72 is configured for coupling with the base 34 and sliding relative to the base and the syringe to guide the shield during longitudinal movement of the shield. In the embodiment shown, the arm 72 has distal end 74 coupled to the side wall of the shield 36 and a proximal end 76. A thumb tab 78 is formed on the proximal end 76 for manipulating the shield and manually pushing the shield in a distal direction relative to the syringe and needle. Ribs 80 project from opposite sides of the arm and extend longitudinally for mating with the flanges 44 on the side walls 42 of the base 34. The flanges 44 contact the top face of the ribs 80 to capture the arm 72 in the open passage 43 of the base formed by the side walls 42, the flanges 44, and the bottom wall 46. The arm is able to slide in the passage 43 with respect to the base in a longitudinal direction relative to the syringe and the needle. In the embodiment shown, the arm 72 has a substantially straight distal portion 82 and an angled proximal portion 84.

The arm 72 includes a locking member to mate with the locking member on the base 34 to retain the shield in selected positions with respect to the base and the syringe and to lock the shield in an extended position to cover the distal end of the needle after use and prevent re-use of the syringe. The locking member includes a mechanism that mates with the spring finger 48 of the base 34. A locking mechanism is positioned at the distal end of the arm 72 near the shield 36 for retaining the shield in a first position and releasing the shield when a force is applied to the end of the arm to allow the arm to slide in the base in a distal direction. The locking mechanism in the embodiment shown has a recessed portion 86 for mating with the tab 52 on the spring finger 48. The recessed portion 86 in one embodiment is formed by a first detent 88 and a second detent 90 spaced from the first detent 88. In other embodiments the recessed portion can be formed in a surface of the arm. The locking mechanism is formed by the detent 88, recess 86, and detent 90.

The first detent 88 is spaced from a distal surface 91 of a radial rib 93 extending from the shield 36 as shown in FIG. 2 to form a recessed area 95. The first detent 88 has a leading distal face 92 that is inclined relative to the longitudinal axis of the arm 72 and a trailing proximal face 94. The proximal face 94 is shown as being at an incline complementing the incline of the surface 54 of the spring finger 48, although the proximal face can be substantially perpendicular to the face of the arm. The proximal face 94 has a shape and configuration for mating with the distal face 54 of the finger 48. The second detent 90 has a configuration to form the recessed portion 86 and is spaced from the first detent 88 a distance to receive the tab 52 of the finger. The second detent 90 has a leading distal face 96 and a proximal face 98.

The second detent 90 can have a suitable configuration to allow the tab 52 of the finger 48 to slide over the second detent 90 by applying sufficient force to the arm in the distal direction. The leading distal face 96 of the detent 90 has a surface with a configuration to allow the finger to slide over the detent in the distal direction. The trailing proximal face 98 of the detent 90 can have a suitable configuration to limit the sliding of the arm over the finger 48 in a proximal direction toward the proximal end of the base to resist sliding in the proximal direction. In the embodiment shown, the second detent 90 has a rounded distal face 96 and a rounded proximal face 98 to slide over the spring finger 48 when a force is applied in the distal direction. The recessed portion 86 is configured to receive the tab 52 of the spring finger 48 when the shield 36 and arm 72 are in an intermediate position with respect to the base and syringe as shown in FIG. 7 relative to the initial position shown in FIG. 6.

A second locking member on the arm mates with the spring finger 48 to lock the arm in an extended position to cover the distal end of the needle after use. The second locking member includes a projection or detent 100 spaced from the first locking mechanism and is positioned toward the proximal end of the arm and proximal to the first locking mechanism. The detent 100 has an inclined distal face 102 and proximal face 104. The inclined distal face 102 has a length to enable the spring finger 48 to slide upward onto the surface of the distal face by applying an axial force to the proximal end of the arm 72. The proximal face 104 in the embodiment shown is angled to engage the tab 52 of the spring finger 48 and prevent the arm 72 from sliding rearward in a proximal direction relative to the base 34 and the syringe to lock the shield in the extended position to cover the tip of the needle. The arm 72 has a longitudinal length to slide distally with respect to the syringe a distance to cover the distal end of the needle.

Figure 6:
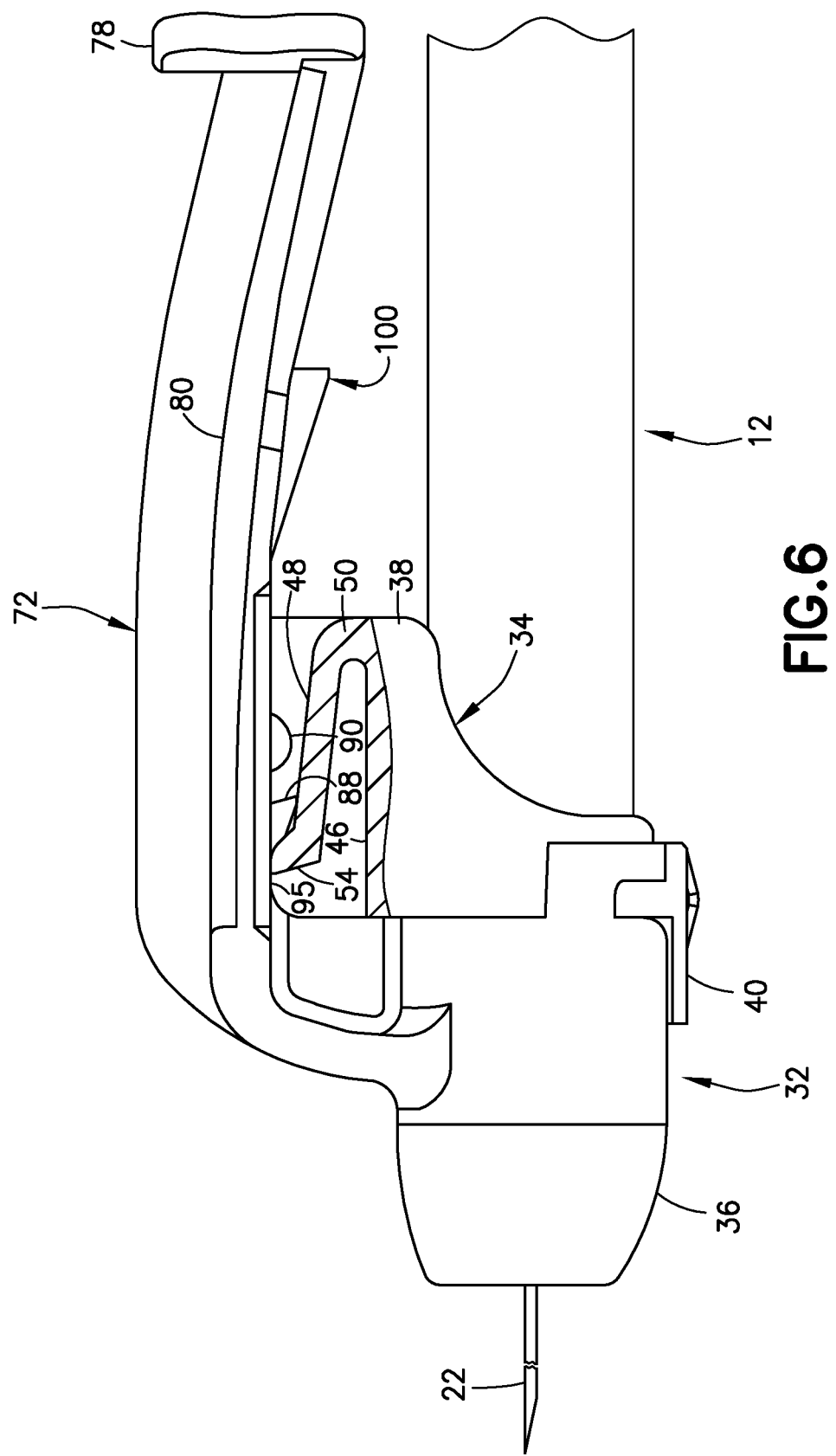
FIG. 6 is a partial cross-sectional side view of the shield in the position of FIG. 5.

During use, the base 34 is coupled to the syringe as shown in FIG. 5 where the base 34 is connected to the distal end of the syringe and the shield 36 is in the retracted position. In the retracted position, the distal end of the body of the sleeve 40 is received in the proximal open end of the shield 36. The needle projects from the distal end of the shield as shown in FIG. 5 and FIG. 6 a distance for filling the syringe and injecting the medication to the patient. The tab 56 of the spring finger 48 is received in the recessed area 95 of the shield when the shield 36 is the proximal position relative to the syringe. In one embodiment, the needle has an exposed length of about 6-8 mm extending from the distal end of the shield 36 when the shield is in the initial retracted, proximal position shown in FIG. 5 and FIG. 6. In one embodiment, the needle has an exposed length of about 6 mm when the shield is in the proximal retracted position. In the retracted position, the tab 52 of the spring finger 48 is positioned forward or distally of the detent 88 to retain the shield in the retracted position. The syringe can be used in the configuration of FIGS. 5 and 6 where the shield 36 forms a limiter to limit the depth of penetration of the exposed length of the needle. The needle 22 has an exposed length extending from the shield when the shield is in the proximal position shown in FIG. 6 to enable the syringe to be filled by piercing a septum of a vial. Needle length less than 6 mm are general difficult to fill from a vial since the needle length may not be sufficient to pierce the septum, particularly when the needle penetrates the septum at an angle. Thus, in the embodiment shown, the needle has an exposed length of at least 6 mm when the shield is in the proximal position.

After filling the syringe, the shield 36 can slide to the second intermediate position shown in FIG. 7 by the user pushing in a distal direction on the proximal end of the arm 72. The inclined leading surface 92 of the detent 88 slides over the proximal face 56 of the tab 52 of the spring finger 48 thereby deflecting the spring finger toward the base where the tab 52 snaps into the recess 86. Sliding the tab 52 into the recess 86 can produce an audible or tactile sensation to the user to provide an indication that the shield is in the second intermediate position shown in FIG. 7. In one embodiment, the exposed length of the needle extending from the shield is about 4 mm to about 5 mm and typically about 4 mm when the shield is in the intermediate position of FIG. 7. In other embodiments, the needle has an exposed length of about 3-5 mm when the shield is in the intermediate position of FIG. 7. The exposed length of the needle is determined by the position of the recess 86 with respect to the arm. The needle shield also forms a limiter to limit the axial length of the exposed portion of the needle during the injection. The recessed portion 86 captures the tab 52 on the finger 48 with sufficient resistance to retain the shield and the arm in the intermediate position during use.

After the injection, the arm 72 is pushed forward in the distal direction with respect to the syringe where the tab 52 separates from the recess position 86 and slides over the second detent 90. The detent 100 slides over the tab 52 of the spring finger to the position shown in FIG. 8 and the shield slides to a position to cover the distal end of the needle. The proximal portion 84 of the arm 72 is at an angle relative to the distal portion 82 to move the shield off center from the needle as shown in FIG. 8 so that distal tip of the needle is no longer aligned with the opening 66 in the end wall of the shield. The distal face 54 of the tab 52 engages the proximal face of the detent 100 to lock the shield in the extended position to cover the end of the needle and prevent re-use of the syringe.

Figure 9:
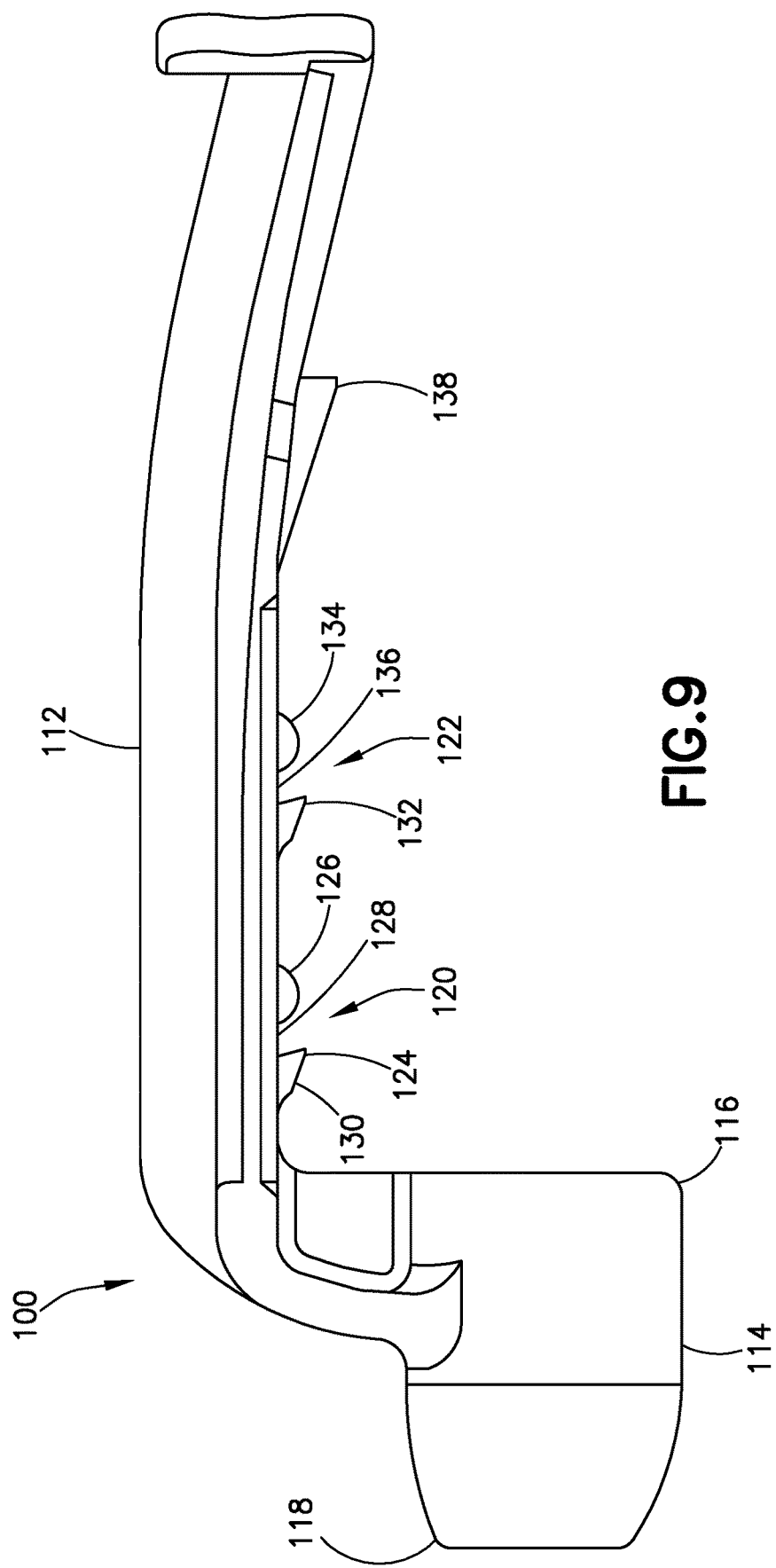
FIG. 9 is a side view of the shield in a further embodiment.

Another embodiment shown in FIG. 9 includes a shield 110 that is similar to the shield of the previous embodiment. The shield 110 includes an arm 112 and sleeve 114 coupled to the arm for covering the end of the needle as in the previous embodiment. The shield 110 is coupled to a base 34 as in the previous embodiment for sliding movement on the base in a linear direction relative to the syringe and the needle. The sleeve 114 has an open proximal end 116 with a dimension for receiving the distal end of the needle hub of the syringe and an open distal end 118 for allowing the needle to project a distance for injecting the medication to the patient.

The arm 112 in the embodiment of FIG. 9 is similar to the arm of the previous embodiment except for including more than one set of detents forming locking mechanisms for positioning the shield at selected locations with respect to the needle hub and needle for exposing different lengths of needle depending on the intended depth of penetration of the needle. The arm 112 has a first locking mechanism 120 at the distal end of the arm 112 and a second locking mechanism 122 spaced proximally from the first locking mechanism 120. The first locking mechanism and the second locking mechanism are configured for mating with the spring finger 48 to retain the shield in a selected position relative to the base 34 and the syringe. The first locking mechanism 120 includes a distal detent 124 and proximal detent 126 that are spaced apart to form a recess 128. The distal detent 124 has an inclined leading distal face 130 for sliding over the spring finger and a trailing proximal face to prevent the shield from sliding proximally relative to the base. The recess 128 has a dimension sufficient to receive the tab of the spring finger to retain the shield in a selected position during use. The second locking mechanism 122 is similar and includes a distal detent 132 and a proximal detent 134 forming a recess 136. The detents are substantially similar to capture the tab of the spring finger and retain the shield in a selected position relative to the base and the syringe.

During use, the shield 110 is received in the opening in the base 34 and positioned in a retracted position to expose a first length of the needle where the syringe can be aspirated and filled with the medication. The syringe can be used by inserting the needle into the patient to inject the medication to a depth corresponding to the exposed length of the needle. The shield can be retracted to a first extended position by sliding the shield distally with respect to the syringe until the spring finger snaps into the recess 128 to retain the shield in the partially extended position to expose a length of the needle that is shorter than the initial exposed length. By way of example, the initial exposed length of the needle can be about 6 mm and exposed length of the needle can be about 4 mm in the partially extended position. The shield can be extended to a second position where the finger is received in the recess 128 of the second locking mechanism 122 to expose a shorter length of the needle that is less than the initial length and less than the length when the spring finger is received in the recess of the first locking mechanism 120. The exposed length of the needle when the spring finger is received in the recess of the second locking mechanism can be, for example, about 2 mm. After use, the shield slides to the extended distal position where shield covers the end of the needle and the proximal locking detent 138 locks the arm and shield in the extended position to prevent re-use in a manner similar to the previous embodiment.

The foregoing embodiments and advantages are exemplary and are not intended to limit the scope of the invention. The description of alternative embodiments are intended to be illustrative, and not to limit the scope of the present invention. Various modifications, alternatives, and variations will be apparent to those skilled in the art, and are intended to fall within the scope of the invention. It is particularly noted that the features of different embodiments and claims may be combined with each other as long as they do not contradict each other. Accordingly all such modifications are intended to be included within the scope of this invention as defined in the appended claims and their equivalents.

The invention claimed is:

1. A syringe assembly comprising:
 a syringe having a proximal end and a distal end, a needle extending from said distal end of said syringe; and
 a shield positioned on said syringe for sliding between a first position where said needle is exposed a first length for filling said syringe, a second position for exposing a second length of said needle that is less than said first length where a locking mechanism retains the shield in the first position, second position, and a third position for covering said needle where the locking mechanism locks the shield in the third position;

a base having a sleeve having a first longitudinal passage for coupling to the syringe and a body for movably receiving the shield, the body having a second longitudinal passage, a spring biased finger in said second longitudinal passage, said spring biased finger having a distal end extending toward a distal end of the base and configured to bend inwardly relative to said base;

said shield having an arm extending from a proximal end of said shield, said arm received in said second longitudinal passage of said body for sliding relative to said base, said arm having a recessed portion on an inner surface at a distal end of said arm for receiving said distal end of said spring biased arm finger of said base to retain said shield in the second position.

2. The syringe assembly of claim 1, where said recessed portion is configured for locking said shield in the second position and allowing said shield to slide to the third position, and for locking said shield in the third position to cover said needle and prevent sliding toward the proximal end of said syringe.

3. The syringe assembly of claim 2, wherein said sleeve of said base is coupled to a needle hub on said distal end of said syringe, and where said base is rotatable with respect to said syringe.

4. A syringe assembly comprising:
a syringe having a proximal end and a distal end, a needle extending from said distal end of said syringe;
a shield positioned on said syringe for sliding between a first position where said needle is exposed a first length for filling said syringe, a second position for exposing a second length of said needle that is less than said first length where a locking mechanism retains the shield in the first position, second position, and a third position for covering said needle where the locking mechanism locks the shield in the third position; and
a base having a body and a sleeve for coupling to the syringe, the base having a longitudinal passage, a spring biased finger in said longitudinal passage, said spring biased finger having a distal end extending toward a distal end of the base and configured to bend inwardly relative to said base;
said shield having an arm extending from a proximal end of said shield, said arm received in said longitudinal passage of said base for sliding relative to said base, said arm having a recessed portion on an inner surface at a distal end of said arm for receiving said distal end of said spring biased arm finger of said base to retain said shield in the second position;
where said locking mechanism comprises said spring biased finger on said base to mate with the arm of said shield to retain said shield in said first position, retain said shield in said second position where said shield is releasable from said spring biased finger in the second position, and to lock said shield in said third position to prevent said shield from moving in a proximal direction with respect to said syringe.

5. The syringe assembly of claim 4, wherein said spring biased finger is biased outwardly from said base for engaging the arm of said shield.

6. The syringe assembly of claim 5, wherein said spring biased finger has a spring hinge at a proximal end of said base for biasing said finger outwardly from said base.

7. The syringe assembly of claim 1, wherein said arm includes a plurality of spaced apart detents on the inner surface of the arm, and the spring biased finger on the base configured for selectively engaging one of said detents on said arm to retain said shield in the first position, second position and third position.

8. A syringe assembly comprising:
a syringe having a proximal end and a distal end, a needle extending from said distal end of said syringe;
a shield positioned on said syringe for sliding between a first position where said needle is exposed a first length for filling said syringe, a second position for exposing a second length of said needle that is less than said first length where a locking mechanism retains the shield in the first position, second position, and a third position for covering said needle where the locking mechanism locks the shield in the third position; and
a base having a body and a sleeve for coupling to the syringe, the base having a longitudinal passage, a spring biased finger in said longitudinal passage, said spring biased finger having a distal end extending toward a distal end of the base and configured to bend inwardly relative to said base;
said shield having an arm extending from a proximal end of said shield, said arm received in said longitudinal passage of said base for sliding relative to said base, said arm having a recessed portion on an inner surface at a distal end of said arm for receiving said distal end of said spring biased arm finger of said base to retain said shield in the second position;
wherein said arm includes a plurality of spaced apart detents on the inner surface of the arm, and the spring biased finger on the base configured for selectively engaging one of said detents on said arm to retain said shield in the first position, second position and third position; and
wherein said plurality of detents on said arm comprises a first detent at a distal end of said arm, and where said spring biased finger of said base releaseably engages said first detent to retain said shield in said first position where said first length of said needle is exposed, and a second detent spaced proximally from said first detent and where said spring biased finger of said base engages said second detent on said arm to retain said shield in said second position, and where said second detent slides over said spring biased finger of said base to a position to lock said shield in said third position whereby said shield body covers a distal end of said needle.

9. The syringe assembly of claim 8, wherein said first detent has an inclined distal face and a proximal face configured to engage said spring biased finger of said base and prevent sliding movement of said shield proximally relative to said syringe, and said second detent spaced proximally from said first detent and defining said recessed portion to retain said shield in said second position, said second detent having an inclined distal face to enable said shield to slide distally with respect to said syringe to a third position, and a third detent on said inner surface of said arm at a proximal end of said arm.

10. The syringe assembly of claim 9, wherein said third detent has an inclined distal surface to slide over said spring biased finger and a proximal surface oriented to engage said distal end of said spring biased finger of said base to lock said shield in the extended third position.

* * * * *